US006875201B1

(12) United States Patent
Kawashima et al.

(10) Patent No.: US 6,875,201 B1
(45) Date of Patent: Apr. 5, 2005

(54) RECESSED PART FORMING INSTILLATION CONTAINER

(75) Inventors: Yoichi Kawashima, Higashiyodogawa-ku (JP); Yukio Kusu, Higashiyodogawa-ku (JP); Hiroshi Yamada, Higashiyodogawa-ku (JP)

(73) Assignee: Santen Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 10/049,694

(22) PCT Filed: Aug. 14, 2000

(86) PCT No.: PCT/JP00/05458

§ 371 (c)(1), (2), (4) Date: Jun. 13, 2002

(87) PCT Pub. No.: WO01/12125

PCT Pub. Date: Feb. 22, 2001

(30) Foreign Application Priority Data

Aug. 17, 1999 (JP) .......................................... 11/230652

(51) Int. Cl.[7] ............................ A61J 1/05; B65D 83/00

(52) U.S. Cl. ....................... 604/295; 604/212; 604/298; 222/205; 222/212; 215/381; 215/384; 220/675

(58) Field of Search ................................ 215/381, 383, 215/384, 382; 222/212, 107, 420, 205, 206; 220/669, 675; 604/312, 216, 295, 298

(56) References Cited

U.S. PATENT DOCUMENTS

| | | | | | |
|---|---|---|---|---|---|
| 2,688,424 | A | * | 9/1954 | Keiter | 222/215 |
| 3,366,284 | A | * | 1/1968 | Marona et al. | 426/94 |
| 3,552,605 | A | * | 1/1971 | Hein | 222/207 |
| 4,787,536 | A | * | 11/1988 | Widerstrom | 222/212 |
| 5,356,052 | A | * | 10/1994 | Poynter | 222/420 |
| 5,462,200 | A | * | 10/1995 | Weiler | 222/83 |
| 5,624,057 | A | * | 4/1997 | Lifshey | 222/212 |
| 5,649,648 | A | * | 7/1997 | Lier et al. | 222/206 |

FOREIGN PATENT DOCUMENTS

| | | | | |
|---|---|---|---|---|
| EP | 0312725 | | | 4/1989 |
| EP | 0566301 | A | * | 10/1993 |
| JP | 153975 | | | 4/1940 |
| JP | 3922583 | | | 8/1964 |
| JP | 509271982 | | | 10/1983 |
| JP | 544134 | | | 6/1993 |
| JP | 255971992 | | | 1/1994 |

* cited by examiner

*Primary Examiner*—Sue A. Weaver
(74) *Attorney, Agent, or Firm*—Webb Ziesenheim Logsdon Orkin & Hanson, P.C.

(57) ABSTRACT

In an eye drops container, a barrel portion 2 in the form of a flexible hollow cylinder defines a dent portion 7 which can be gripped with two fingers.

20 Claims, 8 Drawing Sheets

(PRIOR ART)

RECESSED PART FORMING INSTILLATION CONTAINER

TECHNICAL FIELD

The present invention relates to an eye drops container for containing a solution of medicine therein, and more particularly to an eye drops container composed of a hollow cylinder having flexibility at least at a barrel portion thereof.

BACKGROUND ART

As conventional eye drops containers, especially eye drops containers for medical use, hollow cylindrical containers are widely in use. For instance, a container composed of a hollow cylindrical container body with an inner nozzle tip attached thereto and a container unitary molded a barrel portion of its container body and a liquid instilling portion by means of the blow molding method or vacuum molding method are currently available (see Japanese published utility model gazette No. Sho. 39-11991 for example). Further, as material forming the container, soft thermoplastic resin is generally employed for readiness of its molding.

With the eye drops containers of the above-noted type, for instilling the solution of medicine from the container, the barrel portion of the container will be gripped with two fingers and then the container will be held still at an instilling posture with the instilling nozzle facing an eye to be dispensed with the medicine. Kept under this posture, the barrel portion of the container will be pressed toward the center axis of the container body, thereby to supply a drop of the solution of medicine from the instilling nozzle of the container.

For facilitating the pressing action above, the cylindrical hollow container body is formed of soft thermoplastic resin. However, a person with weak physical strength for the pressing action, such as an aged person, will often find it difficult to control the pressing action. Further, such person with weak gripping strength, such as an aged person, may find it difficult also to maintain the finger gripping position in a stable manner.

The present invention has been made in view of the above-described state of the art and its primary object is to provide a handier eye drops container which provides superior "squeezability" and greater gripping ease through simple and inexpensive modification in the barrel portion of the container.

DISCLOSURE OF THE INVENTION

According to the characterizing feature of an eye drops container having a dent portion relating to claim 1, the container includes a flexible hollow cylindrical barrel portion defining a dent portion which can be gripped with two fingers.

With the above-described characterizing feature, in instilling the solution of medicine from the container body, the dent portion defined in the barrel portion of the container will be gripped with two fingers, so that the gripping position at the tips of the fingers may be maintained in a stable manner. Moreover, when the barrel portion of the container is pressed, the part of this barrel portion contacting the finger tips is dented in advance, so that the force required for the pressing action may be reduced, compared with a case where the part of the cylindrical barrel portion has to be deformed against the elastic resilience.

Accordingly, although the arrangement comprises the simple and inexpensive modification of forming a dent portion in the hollow cylindrical barrel portion, the eye drops container is easier to be gripped and provides superior squeezability with reduced pressing force required. Consequently, there has been achieved an eye drops container having a dent portion easier to use which dropper allows accurate and easy instillation of a solution of medicine from the container.

According to the characterizing feature of an eye drops container having a dent portion relating to claim 2, the dent portion comprises flat or substantially flat gripping faces which are formed concave respectively at two peripheral portions of the barrel portion.

With the above feature, when the barrel portion of the container body is to be gripped with two fingers, this is done by gripping the flat or substantially flat gripping faces at the two portions of the barrel portion. Thus, the local feeling of pressure felt by the gripping fingers may be reduced, whereby the gripping ease may be further increased.

According to the characterizing feature of an eye drops container having a dent portion relating to claim 3, the dent portion comprises curved concave gripping faces which are formed concave respectively at two peripheral portions of the barrel portion, each gripping face being progressively closer to a central axis of the container body as the face extends toward the longitudinal center of the central axis.

With the above feature, when the barrel portion of the container body is to be gripped with two fingers, this is done by gripping the curved concave gripping faces which are formed along the curved surfaces of the fingers. Thus, the local feeling of pressure felt by the gripping fingers may be non-existent or substantially non-existent, whereby the gripping ease or comfort may be further increased.

According to the characterizing feature of an eye drops container having a dent portion relating to claim 4, the container body having the barrel portion comprises a container body made of thermoplastic resin material which is filled with liquid simultaneously with its forming operation.

With the above feature, for eye drops containers for medical use of which manufacture cost reduction is required too, the gripping ease and the squeezability may be improved while achieving the manufacture cost reduction required.

BEST MODE OF EMBODYING THE INVENTION

Figure 1:
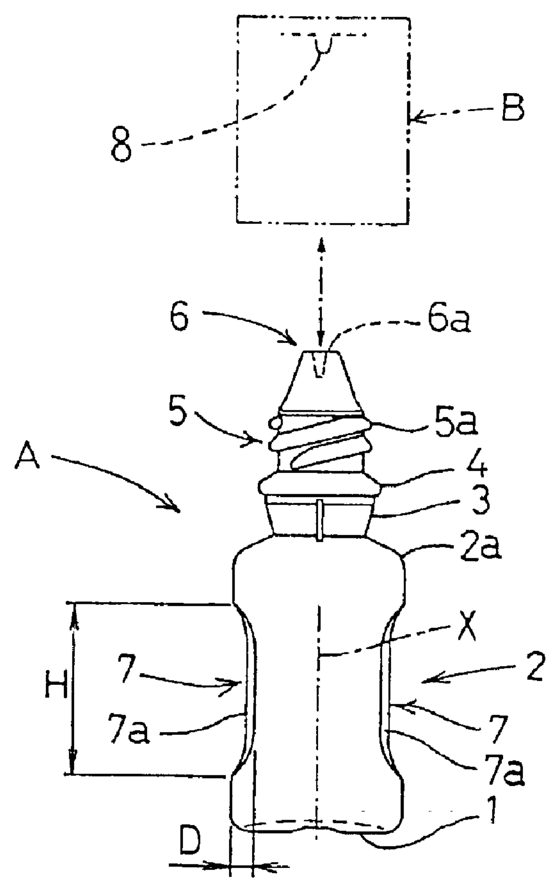
FIG. 1 is a front view of a container body relating to a first embodiment of an eye drops container having a dent portion according to the present invention.
Figure 2:
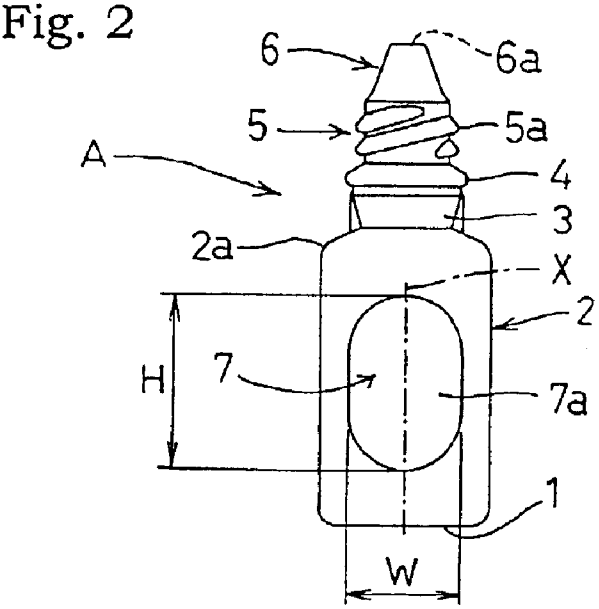
FIG. 2 is a side view of the container body.
Figure 3:
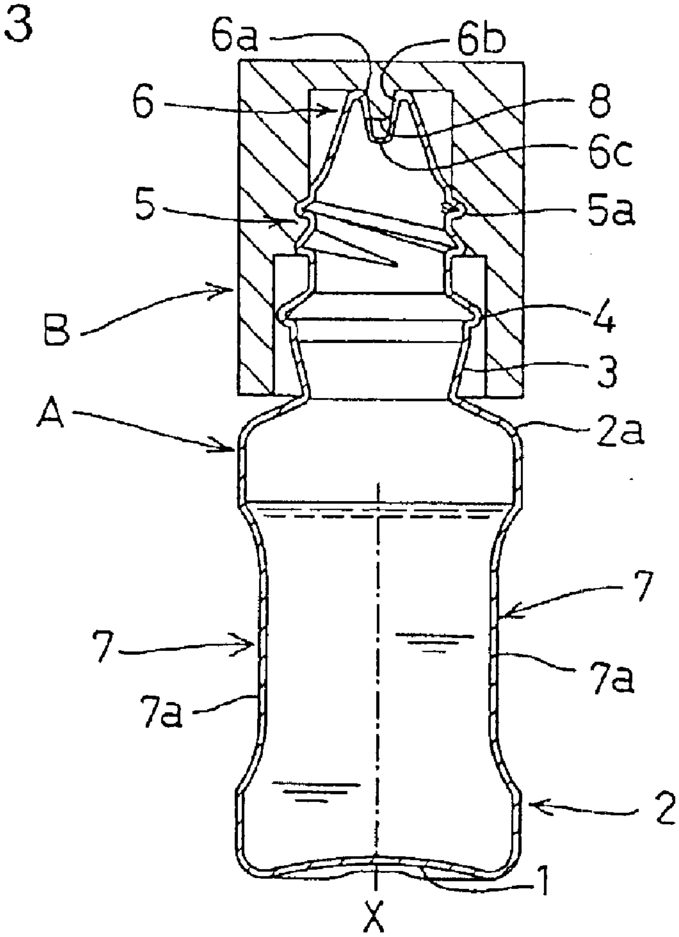
FIG. 3 is a side view in section showing the entire eye drops container.
Figure 4:
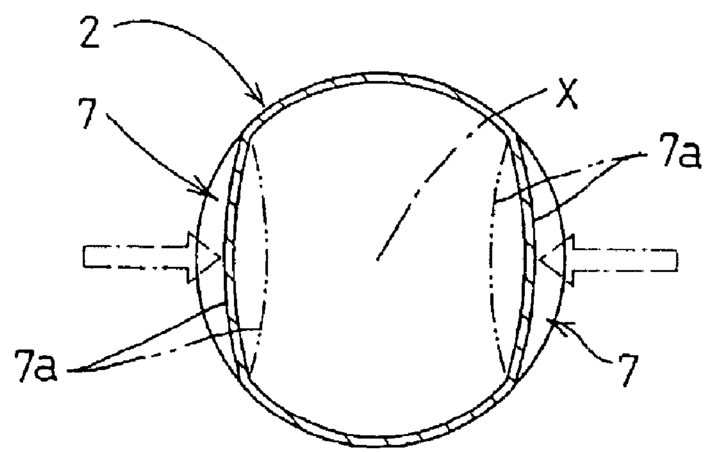
FIG. 4 is a plan view in section showing the container body.
Figure 5:
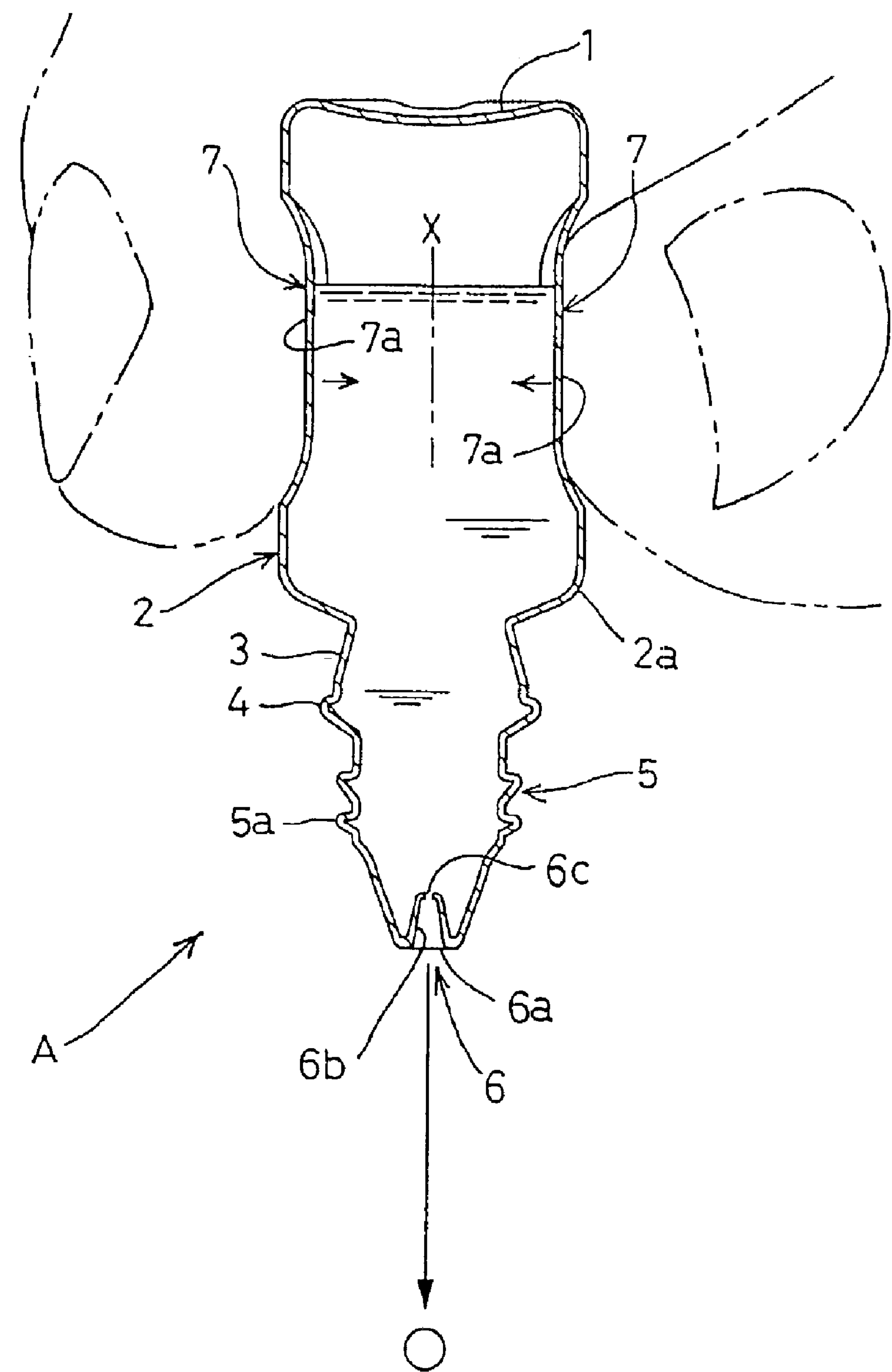
FIG. 5 is a side view in section showing the container body during liquid instilling operation.
Figure 6:
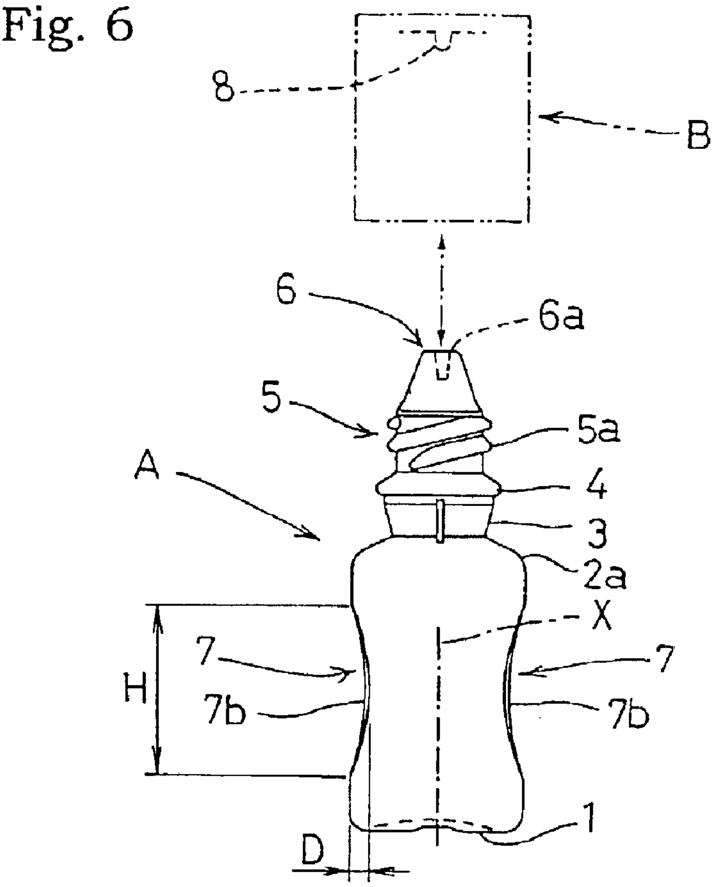
FIG. 6 is a front view of a container body relating to a second mode of embodiment of an eye drops container having a dent portion according to the present invention.
Figure 7:
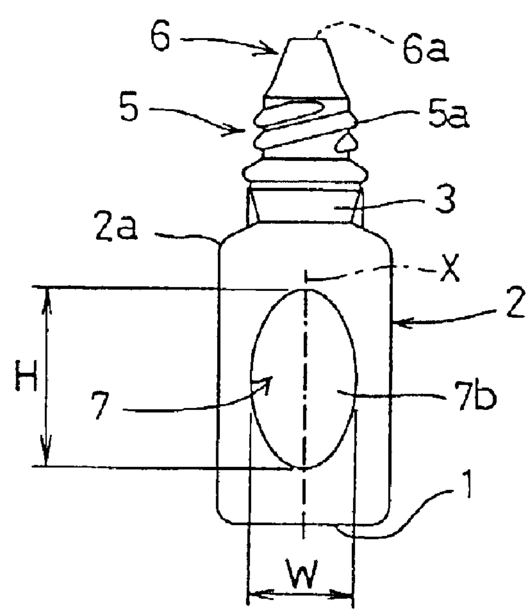
FIG. 7 is a side view of the container body.
Figure 8:
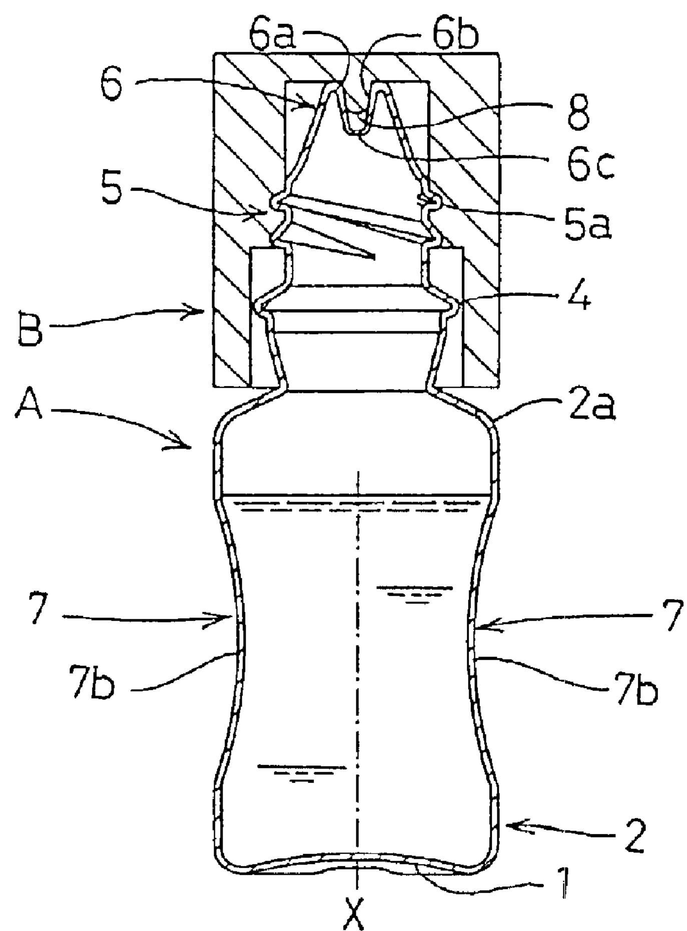
FIG. 8 is a side view in section showing the entire eye drops container.
Figure 9:
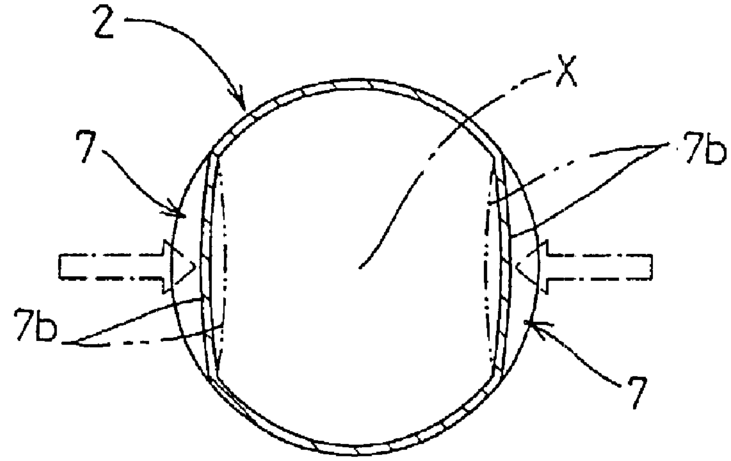
FIG. 9 is a plan view in section showing the container body.
Figure 10:
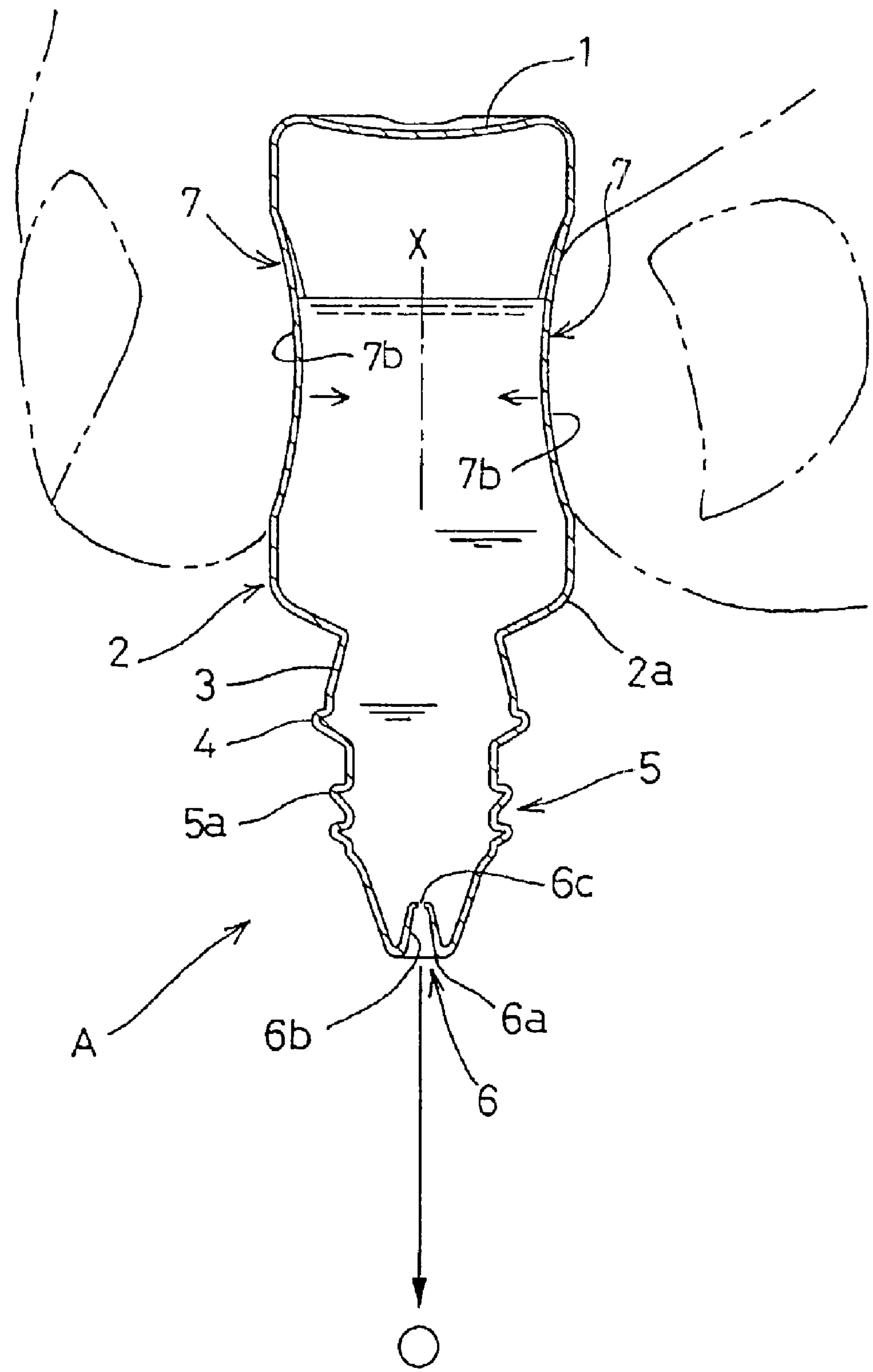
FIG. 10 is a side view in section showing the container body during liquid instilling operation.

For more detailed description thereof, the present invention will be described with reference to accompanying drawings.

[First Mode of Embodiment]

FIGS. 1 through 5 show an eye drops container having a dent portion according to the present invention mainly for use in medical treatment. The dropper includes a container body A made of thermoplastic resin material and charged with a predetermined amount of a solution of medicine therein simultaneously with the blow molding or vacuum molding thereof, and a cap B detachably threaded to a male thread 5*a* of a threaded cylindrical portion 5 of the container body A.

The container body A includes a circular bottom 1 which is curved inwardly, a hollow cylindrical barrel portion 2 extending continuously from its peripheral edge, a cylindrical neck portion 3 extending continuously from a shoulder 2*a* of the barrel portion 2, a circular ring-like stepped portion 4 extending radially outward from an upper portion of the neck portion 3, the threaded cylindrical portion 5 extending continuously and upwardly from the stepped portion and having the male thread 5*a*, and a solution instilling cylindrical portion 6 extending continuously and upwardly from the threaded cylindrical portion and having a instilling nozzle 6*a*.

The thermoplastic resin material forming this container body A can be polyethylene, polyethylene-polypropylene, polypropylene, polyethylene terephthalate, polycarbonate, etc. Thus, the entire formed container body A can be elastically deformed.

The solution instilling cylindrical portion 6 of the container body A defines a recess 6*b* in the form of a conical recess with a bottom, the recess having a progressively increasing inner diameter toward the instilling nozzle 6*a*. In the bottom face of this recess 6*b*, there is formed a small instilling nozzle hole 6*c* which allows control of a solution instilling amount to be pushed out of the container body A in association of a pressing action on the barrel portion 2 with fingers to a predetermined amount.

The recess 6*b* has a depth ranging between 2 mm and 7 mm, preferably between 5 mm and 7 mm, and most preferably 6 mm. Also, the aperture (aperture diameter) of the liquid outlet 6*a* may be adjusted within a range of $\phi$2.0 mm to $\phi$4.0 mm, depending on the property of the solution of medicine.

Specifically, in order to maintain one instilling amount constant, for a solution of medicine having a large surface tension, the aperture of the instilling nozzle 6*a* will be reduced. For a solution having a small surface tension, the aperture of the instilling nozzle 6*a* will be increased.

Further, the instilling nozzle hole 6*c* is formed by using a needle having a diameter ranging between $\phi$0.1 mm and $\phi$0.8 mm. The smaller the diameter of this needle is the better. And, a diameter of about $\phi$0.2 mm is most preferred. However, if it is too small, this will present technical difficulty. Therefore, in actuality, a needle in the range from $\phi$0.4 mm to $\phi$0.6 mm is employed.

The barrel portion 2 of the container body A forms a dent portion 7 which can be gripped with two fingers. Further, this dent portion 7 comprises a pair of gripping faces 7*a* which are formed as flat or substantially flat recesses provided at two peripheral portions of the barrel portion 2 and at two regions opposing to each other across an axis X of the container.

Each gripping face 7*a* is formed as a mildly curved portion having a curvature smaller than that of the remaining portion of the barrel portion 2 when viewed along the direction of the container axis X. Further, when viewed in the radial direction (viewed from its front) normal to the container axis X direction, the gripping face has an intermediate portion excluding the opposed ends in the container axis X direction which intermediate portion is formed straight parallel with the container axis X.

The cap B integrally forms a plug-like projection 8 which is engaged into the recess 6*b* of the container body A for sealing when the cap is threaded on the male thread 5*a* of the container body A.

[Second Mode of Embodiment]

FIGS. 6 through 10 show a modified embodiment of the dent portion 7 formed in the barrel portion 2 of the container body A to be gripped with two fingers. This modified dent portion comprises a pair of curved gripping faces 7*b* which are formed concave respectively at two peripheral portions of the barrel portion, each gripping face being progressively closer to the container axis X as the face extends toward the longitudinal center of the container axis X.

Specifically, each gripping face 7*b* is formed as a mildly curved portion having a curvature smaller than that of the remaining portion of the barrel portion 2 when viewed along the direction of the container axis X. Further, when viewed in the radial direction (viewed from its front) normal to the container axis X direction, the gripping face is curved so that the gripping face comes progressively closer to the container axis X as the face extends toward the longitudinal center of the container axis X.

Incidentally, the rest of the construction is identical to that of the construction described in the first embodiment. Therefore, its identical portions of the construction are denoted with the identical reference numerals employed in the first embodiment and description thereof will be omitted.

[Third Mode of Embodiment]

Figure 11:
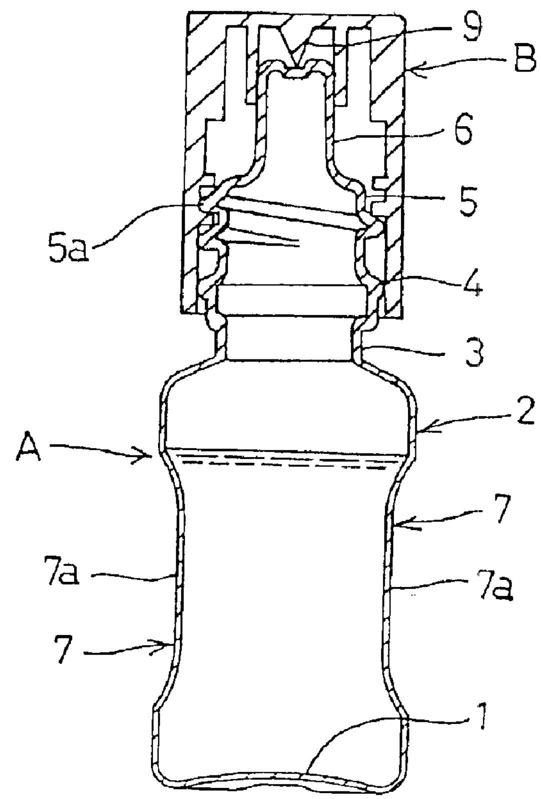
FIG. 11 is an overall front view in section showing a third mode of embodiment of an eye drops container having a dent portion according to the present invention.

In the respective foregoing modes of embodiment, in the solution instilling cylindrical portion 6 of the container body A formed by the blow molding method or vacuum molding method, there are formed, in advance, the recess 6*b* in the form of a cone having a bottom and having a progressively increasing inner diameter toward the instilling nozzle 6*a* and the small instilling nozzle hole 6*c* which allows control of a solution instilling amount to be pushed out of the container body A in association of a pressing action on the barrel portion 2 with fingers to a predetermined amount. The present invention is not limited to such eye drops container. A further construction is possible as shown in FIG. 11, in which a cap B integrally forming a needle-like projection 9 for piercing the instilling nozzle hole at the leading end of the container body A is detachably threaded on a male thread 5*a* of the container body A made of the flexible thermoplastic resin material and charged and sealed with a predetermined amount of a solution of medicine simultaneously with the blow molding or vacuum molding operation. Then, with a threading operation of the cap B to a position one step deeper than its normal closed position, the needle-like projection 9 of the cap B will form a instilling nozzle hole 6*a* at the leading end of the container body A.

Incidentally, the rest of the construction is identical to that of the construction described in the first embodiment. Therefore, its identical portions of the construction are denoted with the identical reference numerals employed in the first embodiment and description thereof will be omitted.

[Fourth Mode of Embodiment]

Figure 12:
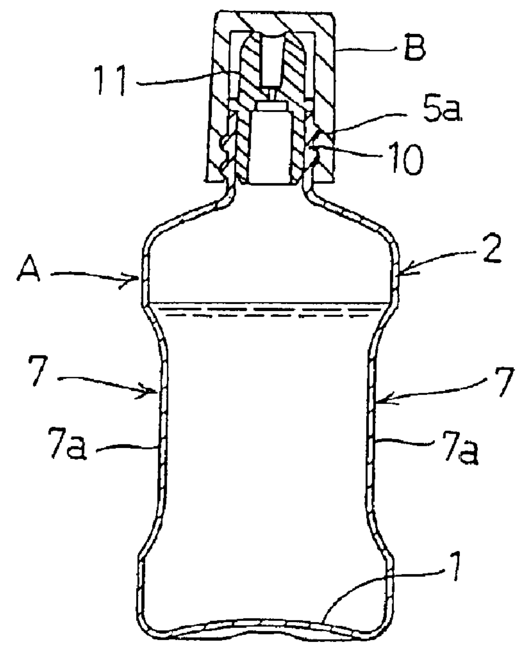
FIG. 12 is an overall front view in section showing a fourth mode of embodiment of an eye drops container having a dent portion according to the present invention.

In the first and second modes of embodiment described above, the container body A of the eye drops container is formed by the blow molding method or vacuum molding method to obtain an inner nozzle tip function. However, the invention is not limited to the eye drops container having such construction. A further construction is shown in FIG. 12, in which an inner nozzle tip 11 formed by the injection molding method is engaged to a cylindrical mouth portion 10 of the container body A.

Incidentally, the rest of the construction is identical to that of the construction described in the first embodiment. Therefore, its identical portions of the construction are denoted with the identical reference numerals employed in the first embodiment and description thereof will be omitted.

[Embodiments]

Two types of eye drops containers having a dent portion in the barrel portion relating to the present invention and an eye drops container in the form of a hollow cylinder not having such dent portion in the barrel portion relating to a comparison example were prepared and the operability of these eye drops containers was studied with regard to their squeezability.

An eye drops container made of polyethylene relating to Embodiment 1 has a configuration corresponding to the container body A according to the first mode of embodiment. Specifically, this polyethylene eye drops container relating to Embodiment 1 has a total length of 56.4 mm in its container axis X direction and its liquid outlet 6*a* has an aperture (aperture diameter) of 2.9 mm. And, its barrel portion 2 is formed as a cylindrical portion with upper end lower ends thereof chamfered, the cylindrical portion having a height of 33.7 mm and a diameter of 19.6 mm. And, in the lateral face of the barrel portion 2, there are formed a pair of dent portions 7 as recesses having a height H of 19.5 mm, a width W of 13.3 mm and a maximum depth D of 1.6 mm (see FIGS. 1 and 2).

An eye drops container made of polyethylene relating to Embodiment 2 has a configuration corresponding to the container body A according to the second mode of embodiment. Specifically, this polyethylene eye drops container relating to Embodiment 2 has a total length of 56.4 mm in its container axis X direction and its instilling nozzle 6*a* has an aperture (aperture diameter) of 2.9 mm. And, its barrel portion 2 is formed as a cylindrical portion with upper end lower ends thereof chamfered, the cylindrical portion having a height of 33.7 mm and a diameter of 19.6 mm. And, in the lateral face of the barrel portion 2, there are formed a pair of dent portions 7 as recesses having a height H of 19.5 mm, a width W of 13.3 mm and a maximum depth D of 1.6 mm (see FIGS. 6 and 7).

Figure 13:
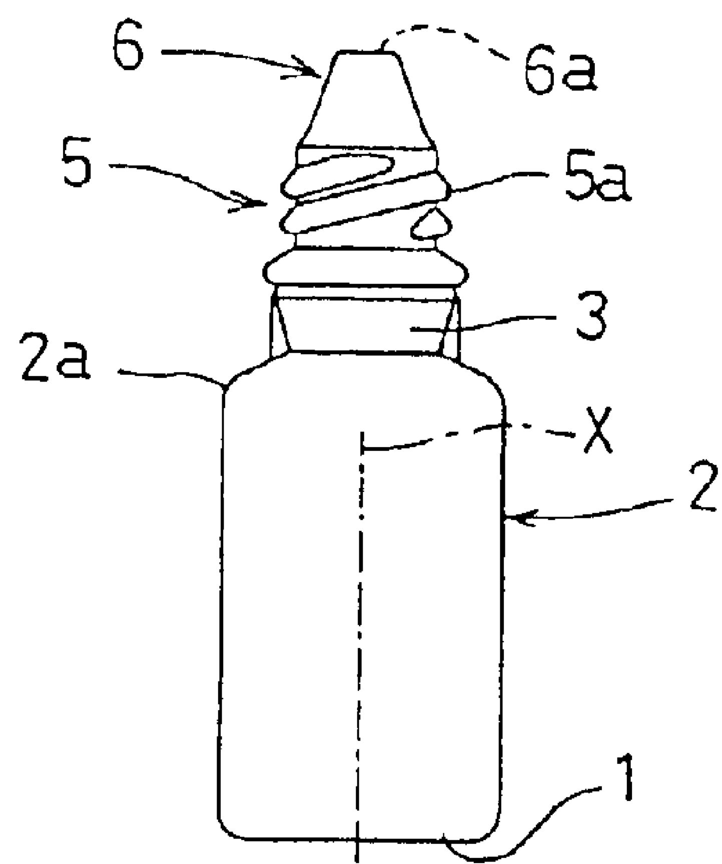
FIG. 13 is a side view showing a container body relating to a comparison example.

A conventional eye drops container made of polyethylene relating to the comparison example, as shown in FIG. 13, includes a barrel portion in the form of a hollow cylinder and has an identical construction to Embodiments 1 and 2, except that no dent portion is provided. Therefore, its identical portions of the construction are denoted with the identical reference numerals employed in the first embodiment and description thereof will be omitted.

These three types of polyethylene eye drops containers are made of a raw material: TOSOH175K (trade name, manufactured by TOSOH Corporation). For obtaining the containers, the raw material was melted and molded so that the containers obtained the weights of 2.0 g, 2.2 g an d 2.4 g, respectively.

Each polyethylene eye drops container (specimen) containing water therein was set at a predetermined position on a measuring device, with the solution instilling cylindrical portion G thereof being oriented downwards. Then, a chip of the squeezability measuring device was placed against the outer surface center of the dent portion 7 (the barrel portion in the case of the comparison example) of this polyethylene eye drops container. After confirming that no water was present inside except for the recess 6*b* of the solution instilling cylindrical portion 6 (that is, no air remained adjacent the instilling nozzle 6*a*), the chip was moved toward the axis of the polyethylene eye drops container to press it and the pressing force required for causing a drop of water to be instilled from the instilling nozzle 6*a* of the polyethylene eye drops container was determined by means of a digital force gauge attached to the measuring device.

In the squeezability tests of the 9 types of polyethylene eye drops containers described above, five specimens was used for each type to conduct 5 tests for each specimen. Average values obtained from these tests are shown in Table 1 below.

TABLE 1 pressing force needed for instillation of one drop of water (unit N)

| container weight (g) | Embodiment 1 | Embodiment 2 | Comparison example |
|---|---|---|---|
| 2.0 | 1.78 | 2.10 | 5.35 |
| 2.2 | 2.39 | 2.60 | 5.93 |
| 2.4 | 3.34 | 3.26 | 6.15 |

From Table 1 above, it may be seen that for all of the Embodiments 1,2 and Comparison example, the greater the container weight of the eye drops container, that is, the greater its wall thickness, the greater the pressing force required for obtaining instillation of one drop of water therefrom.

However, comparison among the containers of a same container weight reveals the following. Namely, with the eye drops containers having the dent portion 7 in the barrel portion 7 relating to the Embodiments 1 and 2, the content (water) can be instilled with a pressing force which ranges from about ⅓ to a ½ of that required for the eye drops container relating to the comparison example, demonstrating that the simple and inexpensive modification provided to the barrel portion of the container body improves the squeezability. With thus improved squeezability, even a person having weak pressing or gripping force can readily manipulate the eye drops container for instilling the solution of medicine contained therein.

[Other Modes of Embodiment]

(1) In the respective modes of embodiments described above, each gripping face 7*a*, 7*b* constituting the dent portion 7 is mildly curved with smaller curvature than that of the remaining portion of the barrel portion 2 as viewed in the container axis X direction. Instead, the invention may be embodied also with forming each gripping face 7*a*, 7*b* as a straight flat face extending tangentially as viewed in the container axis X direction or as a concave curved face which is concave toward the container axis X.

(2) The container body A may be of any construction as long as its barrel portion 2 is provided as a flexible hollow cylindrical portion.

(3) In the respective modes of embodiments described above, the respective gripping faces 7*a*, 7*b* constituting the dent portion 7 are provided at two peripheral regions of the barrel portion 7. Instead, they may be provided at more than three peripheral regions of the barrel portion 2.

INDUSTRIAL APPLICABILITY

The eye drops container having a dent portion according to the present invention may be used as e.g. an eye drops container for use in instilling a solution of eye medicine for medical treatment.

What is claimed is:

1. In an eye drops container of the type having a flexible cylindrical barrel portion, which requires a pressing force of about 5.35 N to about 6.15 N for instilling a single drop of water from the container, the improvement comprising a container having at least one dent portion that can be gripped by two fingers positioned on said cylindrical barrel portion, said at least one dent portion rendering said pressing force required for instilling the single drop of water, wherein said pressing force is about 1.78 to about 3.34 N.

2. The improved eye drops container according to claim 1, wherein the dent portion comprises flat or substantially flat gripping faces which are formed concave respectively at two peripheral portions of the barrel portion.

3. The improved eye drops container according to claim 2, wherein the dent portion comprises curved concave gripping faces which are formed concave respectively at least two peripheral portions of the barrel portion, each gripping face being progressively closer to a central axis of the container body as the face extends toward the longitudinal center of the central axis.

4. The improved eye drops container according to claim 1, wherein the container body having the barrel portion comprises a container body made of thermoplastic resin material which is filled with a solution simultaneously with its forming operation.

5. The improved eye drops container according to claim 2, wherein the container body having the barrel portion comprises a container body made of thermoplastic resin material which is filled with a solution simultaneously with its forming operation.

6. The improved eye drops container according to claim 3, wherein the container body having the barrel portion comprises a container body made of thermoplastic resin material which is filled with a solution simultaneously with its forming operation.

7. The improved eye drops container according to claim 1, wherein said container is made by at least one of-blow molding and vacuum molding.

8. The improved eye drops container according to claim 1, wherein the barrel portion has a height of 33.7 mm and a diameter of 19.6 mm.

9. The improved eye drops container according to claim 1, wherein said dent portion is an oval portion having a height of 19.5 mm and a width of 13.3 mm.

10. The improved eye drops container according to claim 1, wherein the barrel portion comprises a container body made of thermoplastic resin material.

11. The improved eye drops container according to claim 10, wherein the thermoplastic resin material is at least one of polyethylene, polyethylene-polypropylene, polypropylene, polyethylene terephthalate and polycarbonate.

12. The improved eye drops container according to claim 10, wherein the thermoplastic resin is polyethylene.

13. The improved eye drops container according to claim 12, wherein the container weighs between 2.0 g and 2.4 g.

14. The improved eye drops container according to claim 1, wherein the cylindrical barrel portion further comprises a conical recess, with a depth of between 2 mm and 7 mm, having a progressively increasing inner diameter towards the instilling nozzle.

15. The improved eye drops container according to claim 1, further comprising an instilling nozzle having a diameter of between 2 mm and 4 mm.

16. The improved eye drops container according to claim 15, wherein the instilling nozzle includes an instilling nozzle hole having a diameter of between 0.1 mm and 0.8 mm for providing for the instillation of a solution therethrough.

17. A container for eye drops, comprising:

a one-piece elastically deformable plastic barrel portion having sidewalls having an outer surface and an inner surface, a first end and an opposite second end with the first end being a closed end, an axis extending from center of first end to center of second end, the sidewalls of the barrel portion having a first concave wall portion and an opposite second concave wall portion with each of the concave portions having an elliptical shape with an end of long axis of each of the concave portions adjacent and spaced from the first end of the barrel portion and extending toward the second end of the barrel portion, and second opposite end of the long axis of each of the concave portions adjacent to and spaced from the second end of the barrel portion and minor axis of the concave portions generally normal to the major axis of its respective concave portion, the inner surface of the sidewall at the first and second concave portions facing one another, and distance between the first and second concave portions increases as the distance from cross over of the major and minor axis of the concave portions along the major axis increases, and the distance between the inner surface of the sidewalls and the center axis remains substantially constant as the distance from the end of the major axis of the concave portions toward its respective end of the barrel portion decreases; and the second end of the barrel portion having an opening through which fluid passes when the first and second concave portions are moved toward one another.

18. The container for eye drops according to claim 17, wherein the concave portions are equidistant between the first and second ends of the barrel portion and pressing force to move one drop of water through the opening at the second end of the barrel portion when the first and second concave portions are moved toward one another is equal to the pressing force required to move one drop of water through an opening of a reference container having an aperture diameter of 2.9 mm, the reference container made of polyethylene having a total length of 56.4 mm, a barrel portion having a length of 33.7 mm, concave portions having a major axis of 19.5 mm and a minor axis of 13.3 mm, and a maximum depth from the outer surface of the sidewall of 1.6 mm, and a container weight in the range of 2.0 to 2.4 grams, and wherein the pressing force is in the range of about 2.10 to about 3.26N.

19. A container for eye drops, comprising:

a one-piece elastically deformable plastic barrel portion having sidewalls having an outer surface and an inner surface, a first end and an opposite second end with the first end being a closed end, an axis extending from center of first end to center of second end, the sidewalls of the barrel portion having a first concave wall portion and an opposite second concave wall portion with each of the concave portions having an elliptical shape with an end of long axis of each of the concave portions adjacent and spaced from the first end of the barrel portion and extending toward the second end of the barrel portion, and second opposite end of the long axis of each of the concave portions adjacent to and spaced from the second end of the barrel portion and minor axis of the concave portions generally normal to the major axis of its respective concave portion, the inner surface of the sidewall at the first and second concave portions facing one another, and distance between the first and second concave portions substantially constant as the distance from cross over of the major and minor axis of the concave portions along the major axis increases to a transition portion after which the distance between the concave portions increases as the distance along the major axis from the cross over increases, and the distance between the inner surface of the sidewalls and the center axis remains substantially constant as the distance from the end of the major axis of the concave portions toward its respective end of the barrel portion decreases; and the second end of the barrel portion having an opening through which fluid passes when the first and second concave portions are moved toward one another.

20. The container for eye drops according to claim 19, wherein the concave portions are equidistant between the first and second ends of the barrel portion and pressing force to move one drop of water through the opening at the second end of the barrel portion when the first and second concave portions are moved toward one another is equal to the pressing force required to move one drop of water through a reference container having an aperture diameter of 2.9 mm, the reference container made of polyethylene having a total length of 56.4 mm, a barrel portion having a length of 33.7 mm, the concave portions having a major axis of 19.5 mm and a minor axis of 13.3 mm and a maximum depth from the outer surface of the sidewall of 1.6 mm, and a container weight in the range of 2.0 to 2.4 grams, and wherein the pressing force is in the range of about 1.78 to about 3.34N.

* * * * *